(12) United States Patent
Klofta et al.

(10) Patent No.: US 8,466,335 B2
(45) Date of Patent: Jun. 18, 2013

(54) PERSONAL CARE PRODUCT

(75) Inventors: Thomas James Klofta, Cincinnati, OH (US); Gary Dean Lavon, Liberty, OH (US); Thomas Edward Schulte, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 524 days.

(21) Appl. No.: 12/767,320

(22) Filed: Apr. 26, 2010

(65) Prior Publication Data
US 2011/0264059 A1 Oct. 27, 2011

(51) Int. Cl.
*A61F 13/15* (2006.01)
*A61L 9/00* (2006.01)
*A61L 9/04* (2006.01)

(52) U.S. Cl.
USPC .......... 604/367; 604/359; 604/360; 424/76.1; 424/76.4

(58) Field of Classification Search
USPC .. 604/367, 359, 360; 424/76.1–76.4; 222/105
See application file for complete search history.

(56) References Cited

U.S. PATENT DOCUMENTS

| | | | |
|---|---|---|---|
| 2,843,522 A | 7/1958 | Mahon | |
| 3,770,648 A | 11/1973 | Mackles | |
| 3,935,862 A | 2/1976 | Kraskin | |
| 4,034,077 A | 7/1977 | Hill et al. | |
| 4,196,218 A | 4/1980 | Thiele | |
| 4,273,786 A | 6/1981 | Kraskin | |
| 4,278,658 A | 7/1981 | Hooper et al. | |
| 4,329,366 A | 5/1982 | Nashed et al. | |
| 4,389,418 A | 6/1983 | Burton | |
| 4,514,383 A | 4/1985 | Murray et al. | |
| 4,556,560 A | 12/1985 | Buckingham | |
| 4,569,839 A | 2/1986 | Grollier et al. | |
| 4,574,082 A | 3/1986 | Tietjen et al. | |
| 4,672,074 A | 6/1987 | Harendza-Harinxma | |
| 4,725,438 A | 2/1988 | Leazer | |
| 4,800,076 A | 1/1989 | Bhat et al. | |
| 4,816,254 A | 3/1989 | Moss | |
| 4,842,593 A | 6/1989 | Jordan et al. | |
| 4,847,071 A | 7/1989 | Bissett et al. | |
| RE33,107 E | 11/1989 | Dikstein et al. | |
| 4,911,932 A | 3/1990 | Clum et al. | |
| 4,933,330 A | 6/1990 | Jorgensen et al. | |

(Continued)

FOREIGN PATENT DOCUMENTS
EP 1 026 102 A1 8/2000

OTHER PUBLICATIONS

International Search Report, PCT/US2011/033340, mailed Jul. 5, 2011, 6 pages.
U.S. Appl. No. 12/767,283, filed Apr. 26, 2010, Klofta, et al.

(Continued)

*Primary Examiner* — Jacqueline F. Stephens
(74) *Attorney, Agent, or Firm* — Kathleen Y. Carter; John G. Powell

(57) ABSTRACT

A personal care product that includes a personal care composition disposed in a collapsible bag at least partially surrounded by an elastically deformable member and, optionally, an outer container body. The elastic member is constructed of an elastically extensible material that permits the transfer of infrared radiation through at least a portion of the elastic member. Potential energy is generated by stretching the elastically deformable member, which is used to dispense the composition in lieu of a propellant or pump. The container may also include a actuatable valve for dispensing the composition.

17 Claims, 13 Drawing Sheets

U.S. PATENT DOCUMENTS

| | | |
|---|---|---|
| 4,938,960 A | 7/1990 | Ismail |
| 4,996,238 A | 2/1991 | Matravers |
| 4,996,239 A | 2/1991 | Matravers |
| 5,043,359 A | 8/1991 | Ward et al. |
| 5,083,681 A | 1/1992 | Nye |
| 5,085,856 A | 2/1992 | Dunphy et al. |
| 5,137,714 A | 8/1992 | Scott |
| 5,208,031 A | 5/1993 | Kelly |
| 5,210,102 A | 5/1993 | Klimesch |
| 5,232,691 A | 8/1993 | Lemole |
| 5,234,689 A | 8/1993 | Lindauer et al. |
| 5,266,318 A | 11/1993 | Taylor-McCord |
| 5,362,488 A | 11/1994 | Sibley et al. |
| 5,389,204 A | 2/1995 | Ampulski |
| 5,436,007 A | 7/1995 | Hartung et al. |
| 5,527,519 A | 6/1996 | Miksits et al. |
| 5,543,135 A | 8/1996 | Dahms |
| 5,545,673 A | 8/1996 | Kelly |
| 5,558,872 A | 9/1996 | Jones et al. |
| 5,573,753 A | 11/1996 | Tapley |
| 5,576,006 A | 11/1996 | Smith |
| 5,603,863 A | 2/1997 | Dahms |
| 5,616,331 A | 4/1997 | Allard et al. |
| 5,635,191 A | 6/1997 | Roe et al. |
| 5,643,588 A | 7/1997 | Roe et al. |
| 5,652,274 A | 7/1997 | Martin |
| 5,662,937 A | 9/1997 | McCuaig |
| 5,665,426 A | 9/1997 | Krysik et al. |
| 5,730,993 A | 3/1998 | Allard et al. |
| 5,733,895 A | 3/1998 | Forestier et al. |
| 5,744,146 A | 4/1998 | Peters et al. |
| 5,756,082 A | 5/1998 | Cashin et al. |
| 5,756,110 A | 5/1998 | Allard et al. |
| 5,762,945 A | 6/1998 | Ashley |
| 5,776,440 A | 7/1998 | Forestier et al. |
| 5,834,290 A | 11/1998 | Egelrud et al. |
| 5,861,143 A | 1/1999 | Peterson et al. |
| 5,861,144 A | 1/1999 | Peterson et al. |
| 5,861,146 A | 1/1999 | Peterson et al. |
| 5,863,522 A | 1/1999 | Forestier et al. |
| 5,869,061 A | 2/1999 | Brugh |
| 5,869,062 A | 2/1999 | Oliver |
| 5,869,071 A | 2/1999 | Wieselman et al. |
| 5,874,094 A | 2/1999 | Castello |
| 5,885,599 A | 3/1999 | Peterson et al. |
| 5,914,101 A | 6/1999 | Tapley et al. |
| 5,939,053 A | 8/1999 | Forestier et al. |
| 5,945,211 A | 8/1999 | Yamaguchi et al. |
| 5,958,397 A | 9/1999 | Smerbeck et al. |
| 5,961,961 A | 10/1999 | Dobkowski et al. |
| 5,962,441 A | 10/1999 | Blank |
| 5,965,137 A | 10/1999 | Petrus |
| 5,965,610 A | 10/1999 | Modak et al. |
| 5,968,531 A | 10/1999 | Miyoshi et al. |
| 5,972,359 A | 10/1999 | Sine et al. |
| 6,025,411 A * | 2/2000 | Wong et al. .................. 523/120 |
| 2010/0133295 A1* | 6/2010 | Chan et al. ....................... 222/95 |

OTHER PUBLICATIONS

U.S. Appl. 12/767,251, filed Apr. 26, 2010, Klofta, et al.

* cited by examiner

Axial

PERSONAL CARE PRODUCT

FIELD OF THE INVENTION

A personal care product is disclosed. Specifically, a personal care composition contained in a non-pump, non-aerosol, tube-in-sleeve type dispenser, which when dispensed forms a suitable film on a surface without the use of an additional applicator or without the need for additional spreading onto the surface by the user.

BACKGROUND OF THE INVENTION

Undesirable skin conditions associated with dry skin (e.g., redness, itching, burning, peeling, cracking, scaling, flaking) occur in varying degrees and at various times for most humans. These undesirable skin conditions may be particularly evident in winter. Skin care products formulated with at least one active ingredient to address undesirably dry skin are widely known. For example, occlusives such as petrolatum or silicone oils are widely known to inhibit loss of natural moisture by forming a barrier between the epidermis and the environment. Another approach is the use of keratolytic agents such as alpha-hydroxy acids to enhance the rate of dermal exfoliation. A third approach is the topical application of a humectant such as glycerin to help retain moisture in the skin.

Undesirable skin conditions may also be caused by certain fungi (e.g., *Candida albicans*), which are known to attack the skin of humans. Fungal infections may be caused by dermatophytes, which are opportunistic organisms, or yeasts, which may occur naturally on the body. Commonly known types of fungal infections include athletes foot; yeast infections of the hair, skin, fingernails and toenails; jock itch; ringworm; and diaper rash. In particular, fungal infections associated with diaper rash may occur more often in infants or young children who are prescribed antibiotics. The antibiotics may alter the balance between the yeast and the "good" bacteria typically present in the intestine of a human by killing the good bacteria. This imbalance may result in an increased yeast concentration in the intestine and, consequently, more yeast being passed out of the body in the stool. The increased amount of yeast being passed out of the body may attack the skin around the anus, perinea, and/or genitals of the child, causing skin irritation.

Still other undesirable skin conditions may be caused by exposure of the skin to certain enzymes. For example, it is believed that fecal proteolytic and lipolytic enzymes, of intestinal and/or pancreatic origin, may play a direct role in causing diaper rash, which can lead to skin irritation and inflammation. Proteases and lipases are classes of enzymes produced by the body to help degrade proteins and fats in the digestive process. When in contact with the skin of a human, these enzymes are capable of causing skin irritation. Typically, proteases and lipases are neutralized prior to passing out of the body. However, sickness or infection may reduce the body's ability to neutralize these enzymes. As a result, these enzymes may retain a significant amount of enzymatic activity when passed out of the body in the stool. In addition, the irritating effects of fecal enzymatic activity toward the skin may be amplified if urine is present and/or if the skin is occluded, which may occur in diaper wearing individuals. Water, and particularly water in the form of urine, is especially effective at diminishing the barrier property of skin, thereby enhancing the susceptibility of skin to fecal enzyme irritation. An alkaline feces pH is a further contributing factor to enhanced enzymatic activity of feces. For example, it is well known that although the feces of breast-fed babies are usually acidic, the feces of bottle-fed and spoon-fed infants are generally alkaline, with a pH ranging from slightly alkaline (pH 7.2-7.5) to very alkaline (pH 8.7 and above). Thus, bottle-fed and spoon-fed infants in particular may have a propensity to develop diaper rash due to pH-enhanced activity of fecal enzymes.

For babies, the occurrence of diaper rash is not uncommon. To address the cause and/or symptoms associated with diaper rash, a caregiver may apply a commercially available rash cream to the diaper rash affected area of a baby's skin. Although commercial diaper rash creams may be effective for addressing the symptoms and/or causes of diaper rash, at least some caregivers may find they are inconvenient to apply, since such creams typically involve rubbing and/or spreading a thick and/or tacky ointment onto the baby's skin. The rubbing and/or spreading action may cause additional frictional irritation to the skin, and the undesirably transfer of the ointment, for example, to one's hands and/or fingers may lead to the inconvenient and additional steps of cleaning one's hands. Thus, at least some caregivers desire a more convenient means to apply personal care compositions to skin.

A variety of containers and delivery systems have been developed for storing, dispensing, and applying skin care compositions to skin or other surfaces (e.g., human skin, animal skin, substrate surfaces). One well known dispensing system is a simple "squeezable" container. That is, a container formed from a flexible material to which a user can apply pressure by squeezing, thereby reducing the internal volume of the container and forcing the contents of the container out through an opening. However, at least some commonly known squeezable containers expel their contents in a manner that may be hard to control. For example, some commonly known lotion dispensers may initially dispense a "blob" of lotion, but eventually stop dispensing, or worse, begin a sort of "splattering" or "sputtering" of lotion, which may result in contamination of clothing or other surfaces. Because of the inexact method of dispensing the skin care composition out of a squeezable container (i.e., applying too much or too little pressure), a user may not dispense the desired amount of lotion. In addition, it may be necessary for a user to spread the skin care composition over the desired area of the body with a hand or finger, resulting in the undesirable contamination of the hands/fingers and/or discomfort to the irritated, highly sensitive areas of the skin.

Aerosol delivery systems have been widely used to deliver a variety of consumer goods, including skin care compositions because they typically "atomize" the composition, which may reduce the need for spreading the composition over the skin (e.g., with a hand or fingers). Aerosol systems typically utilize volatile propellants to push the product out of a container. Aerosol technology has gained favor for being both effective and relatively inexpensive. But the release of traditionally used fluorocarbon and hydrocarbon type propellants into the atmosphere is undesirable due to the actual and perceived negative impacts these chemicals may have on the environment. Another disadvantage is that the aerosol containers are considered pressure vessels, which can necessitate extra safety equipment and procedures during its manufacture. The pressurized containers can also create concern for human injury if problems arise during storage, use, or disposal. And the high internal pressure accompanying many aerosol products may limit the material and geometry options for the container. Yet another disadvantage is that as the amount of product in the container decreases through normal use, the pressure inside the container typically decreases. In at least some instances, when the container no longer has sufficient pressure to expel the stored product, there may still be a useful amount of product remaining in the container. And when the aerosol container is discarded, the remaining product is wasted or may even result in undesirable environmental pollution. Still another disadvantage of aerosol dispensers is that when used to apply a composition to the skin of a user, the composition tends to be expelled at an undesirably cold temperature and may create a feeling of discomfort on the skin of a user.

A pump system is one alternative to aerosols and squeezable containers. Pump systems generally dispense a metered amount of product by actuating a pump. However, different consumers may not all desire the same amount of product for a particular use, and thus difficulty arises in providing a proper metered amount that is satisfactory to all users. For example, a first consumer may need to pump a dispenser two times to dispense the desired amount of product, while another consumer may only require one pump of the same dispenser. And if the desired amount of product is somewhere between pumps, the consumer may become frustrated in attempting to use the pump dispenser. In addition, pump systems typically must be properly oriented to function as intended. For example, some commonly known pump systems will not function properly when the pump is oriented upside-down or even sideways. And some pump systems may dispense undesirably, intermittently, or not at all as the amount of product in the container is depleted. Further, some pump systems may be better than aerosol containers when it comes to expelling the contents the container, but pump systems may still be unable to expel substantially all of their contents. Finally, some nozzles tend to clog if not used for extended periods of time, especially if the skin care composition contains particulate ingredients.

Accordingly, it would be desirable to provide a skin care composition in a non-pump, non-aerosol dispenser. It would also be desirable to provide a skin care composition in a dispenser capable of dispensing substantially all of the skin care composition. It would further be desirable to provide a skin care product that at least reduces the potential for cloggings issues within the dispenser to occur.

SUMMARY OF THE INVENTION

In order to provide a solution to the problems set forth hereinabove, a new personal care product for applying a personal care composition to skin in the form of a film without the use of an additional applicator is disclosed. The personal care product comprises an outer container and an at least partially expanded collapsible bag disposed in the outer container. The collapsible bag includes an elastic member surrounding at least a portion of the collapsible bag such that the elastic member is stretched axially and radially. The elastic member is constructed of an elastically extensible material that permits the transfer of infrared radiation through at least a portion of the elastic member. The personal care product also includes a personal care composition disposed in the collapsible bag.

DETAILED DESCRIPTION OF THE INVENTION

Figure 1A:
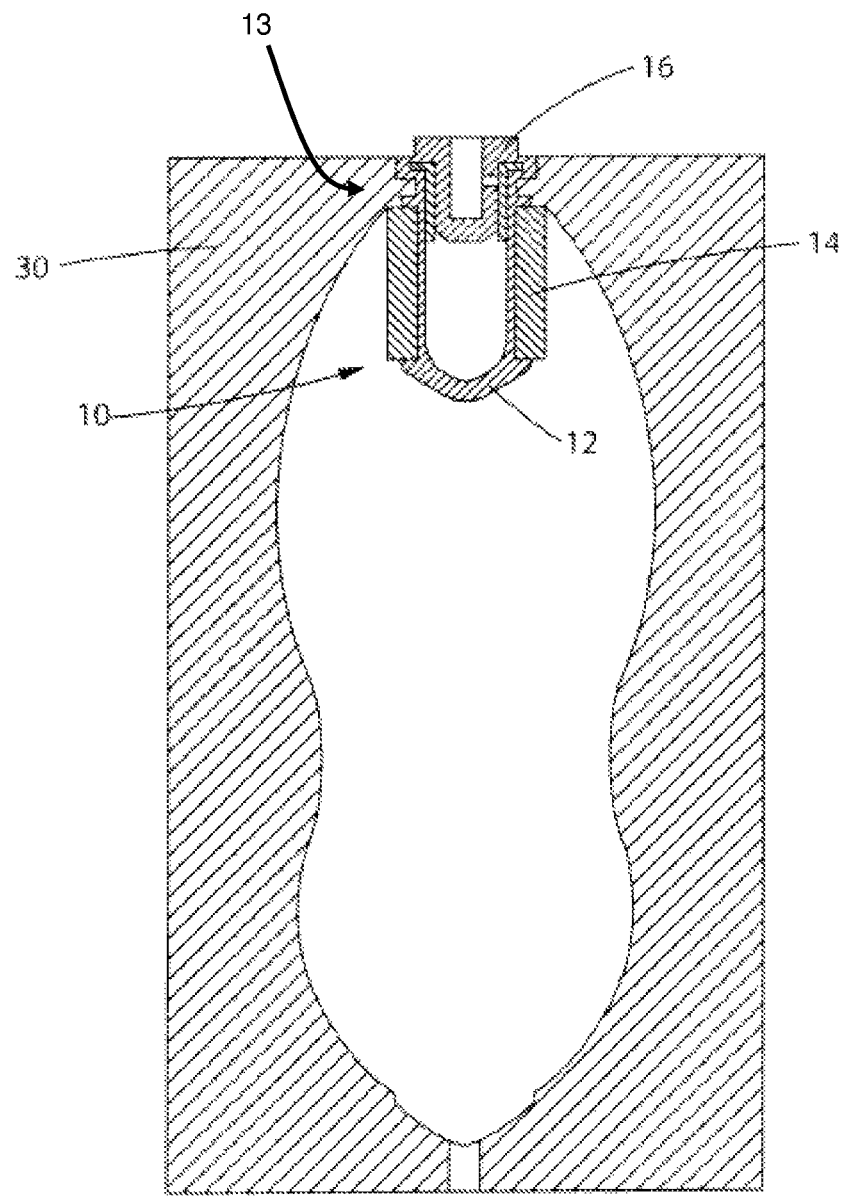
FIGS. 1A-1C are cross-section views of an embodiment of a skin care product.

The present personal care product utilizes an elastically extensible, tube-in-sleeve type of dispenser to provide a convenient and environmentally friendly way to apply a personal care composition to skin. The tube-in-sleeve type dispenser disclosed herein is capable of dispensing substantially all of the skin composition stored therein (e.g., more than 90%; 92%; 93%; 94%; 95%; or, ideally, 100%) and does not require undesirable chemical propellants. Additionally, the present tube-in-sleeve type dispenser is capable of desirably dispensing the stored personal care composition in a variety of container positions (e.g., upside-down, right-side-up, or sideways). Since the present personal care product does not need to be highly pressurized like an aerosol dispenser, the personal care composition may be dispensed at a temperature which is not substantially different than the ambient temperature of the surrounding environment. Surprisingly, it has also been found that the present personal care product provides the unexpected benefit of being substantially cheaper to manufacture than commonly known aerosol and pump dispensers.

Certain properties described herein may include one or more ranges of values. It is to be understood that these ranges include every value within the range, even though the individual values in the range may not be expressly disclosed.

"Axial" means the direction generally corresponding to the lengthwise direction of an article.

"Collapsible" and variations thereof mean that the volume of an article or component (e.g., a collapsible bag or other flexible container) can be reduced by at least 50% but less than 100% (e.g., 60%, 70%, 80%, 90%, 95%, 98%, or even 99%), relative to its volume in an expanded state, by an externally applied pressure of between 100 kPa and 600 kPa (e.g., 200-400 kPa, 260-340 kPa; or even 300 kPa) without substantial degradation of the performance of the article or component or damage to surrounding components that would impair the article's continued use.

"Compromised skin" means skin that is afflicted with a skin ailment such as one or more of the skin ailments disclosed herein.

"Elastic" and "elastically extensible" mean the ability of a material to stretch by at least 50% without rupture or breakage at a given load, and upon release of the load the elastic material or component exhibits at least 80% recovery (i.e., has less than 20% set). For example, an elastic material that has an initial length of 100 mm can stretch to at least 150 mm (50% stretch) and, upon removal of the force, retract to a length of 110 mm (i.e., have a set of 10 mm or 10%). Stretch, sometimes referred to as strain, percent strain, or elongation, along with recovery and set may each be determined according to a suitable hysteresis test commonly known in the art. It is to be understood; however, that this definition of elastic does not apply to materials that do not have the proper dimensions (e.g., not wide enough) to be properly subjected to a suitable hysteresis test. Instead, such material is considered to be elastic if it can stretch to at least 50% upon application of a biasing force, and return substantially to its original length (i.e., exhibit less than 20% set) upon release of the biasing force.

"Expandable" and variations thereof mean that the volume of an article or component (e.g., a polymeric preform or collapsible bag) can be increased by at least 50% up to 1000 times (e.g., 100%; 400%; 800%; 1200%; 2000%; 6000% or more) its volume in a relaxed or collapsed state, without rupture or breakage of the element. For example, a preform may have an initial volume of 10 ml, but when expanded (e.g., by filling with a gas and/or a personal care composition) the volume is increased to 1 liter.

"Extensible" means the ability to stretch or elongate, without rupture or breakage, by at least 50%.

"Film" means a layer or coating that appears to be substantially continuous (i.e., substantially non-porous) when perceived by the human eye at a distance of 45 cm. Exemplary films may have a thickness of between 100 nm and 500 µm. Additionally, exemplary films may have a substantially uniform thickness (i.e., varies by less than 30%).

"Infrared" or "infrared light" ("IR") means electromagnetic radiation having a wavelength of between 700 nanometers ("nm") and 1 millimeter ("mm").

"Joined" means configurations whereby an element is directly secured to another element by affixing the element directly to the other element, and configurations whereby an element is indirectly secured to another element by affixing the element to intermediate member(s) that in turn are affixed to the other element.

"Plastic" and "plastically extensible" mean the ability of a material to stretch by at least 50% without rupture or breakage at a given load and upon release of the load the material or component exhibits at least 20% set (i.e., recovers less than 80%). For example, an extensible material that has an initial length of 100 mm can stretch at least to 150 mm (50% stretch) and, upon removal of the applied force, retract to a length of 35 mm (i.e., have a set of 35 mm (35% set), when subjected to a suitable hysteresis test commonly known in the art.

"Operatively exhausted" means that a composition contained in a container is depleted such that the container is no longer able to dispense the composition as intended. By way of example, a container is initially filled to capacity with a personal care composition (i.e., is 100% full) and then the composition is dispensed until less than 5% of the initial amount, but greater than 0%, remains, at which time the container ceases to dispense any more of the composition. In this example, even though there is still some amount of residual composition remaining in the container, the container is operatively exhausted. It is to be appreciated that a container may be operatively exhausted and still dispense composition, if the composition is not dispensed as intended (e.g., exit pressure is too low, sputtering, dripping and the like). Ideally, the personal care product disclosed herein will dispense substantially all of the composition stored in it before being operatively exhausted.

"Preform" means a material, element, component, or article that has undergone preliminary shaping but is not yet in its final form.

"Radial" means the direction perpendicular to the axial direction, and generally corresponds to the widthwise direction of an article.

"Relaxed" means the state of an element, material or component at rest with substantially no external force acting on the element, other than gravity.

Personal Care Composition

Personal care compositions for use herein are not particularly limited and include, for example, skin care compositions, antifungal compositions, and enzyme inhibiting compositions. Suitable personal care compositions may be in the form of, for example, lotions, creams, pastes, balms, ointments, pomades, gels, liquids, combinations of these and the like, and may also contain solids to further enhance the benefits for the consumer. The personal care compositions disclosed herein include at least one active ingredient. An active ingredient is generally recognized as an ingredient that causes the intended pharmacological effect. For the personal care compositions disclosed herein, the pharmacological effect produced by the active ingredient aids in the treatment and/or prevention of skin ailments related to diaper rash, eczema, cradle cap, fungal infection, hives, head rash, and/or undesirable enzyme activity. For example, an active ingredient may soothe the symptoms associated with diaper rash, help reduce moisture loss from the skin, moisturize the skin, eliminate fungal infection, and/or neutralize enzyme activity. Active ingredient(s) may be present in an amount of between 0.001 and 100% by weight based on the weight of the personal care composition ("wt %"). It is to be appreciated that the amount of active ingredient(s) may include any percentage in this range.

Some skin care compositions are applied to human skin for addressing skin damage related to a lack of moisture (i.e., "dry skin"). Skin care compositions may also address the visual look of the skin (e.g., reduce the appearance of flaky, cracked, and/or red skin) and/or the tactile feel of the skin (e.g., reduce roughness and/or dryness of the skin while improved the softness and subtleness of the skin). Skin care compositions typically include at least one active ingredient for the treatment or prevention of skin ailments like diaper rash or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, and colloidal oatmeal, and combinations of these. Additionally or alternatively, the skin care composition may include one or more natural moisturizing factors ("NMFs"). NMFs are the collection of certain water-soluble compounds found in the stratum corneum of human skin. NMFs typically comprise between 20 and 30% of the dry weight of the corneocyte. NMFs typically absorb water from the atmosphere and combine it with their own water content to allow the outermost layers of the stratum corneum to stay hydrated despite exposure to the elements. But because at least some NMF components are water soluble, they may be easily leached from the cells with water contact, which is one reason why repeated contact with water may actually make the skin drier. While human skin typically includes a lipid layer that surrounds the corneocyte and helps to prevent loss of NMFs, it may be desirable to provide NMFs in a skin care composition to replace at least some of the lost NMFs. NMFs may optionally be included in the present skin care composition in an amount of between 0 and 10 wt %. Suitable examples of NMFs and ingredients employed to help prevent the loss of NMFs from the skin include ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, and sodium PCA (sodium pyrrolidone carboxylate). Other ingredients, which mimic the lipid content of human skin, and thus may be helpful in making dry skin look and feel better, may be included in the present skin care composition and include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, and orange oil.

Antifungal compositions are generally understood to be substances that inhibit or prevent the growth of fungus and/or kill or destroy fungal cells. Antifungal compositions suitable for use herein are not particularly limited, but generally include at least one antifungal agent for providing an antifungal benefit to the skin of a human. The antifungal agent may be present in an amount of between 0.01 and 100 wt %. It is to be appreciated that the amount of antifungal agent(s) may include any percentage in this range. Examples of antifungal agents include, without limitation, polyene antifungal agents (e.g., natamycin, rimocidin, nystatin, amphotericin B, candicin, hamycin); azole antifungal agents (e.g., imidazoles, triazoles, and thiazoles); allylamines; echinocandins; and effective combinations of these. In addition to the foregoing, other compositions that may be useful as an antifungal agent include, benzoic acid in combination with a keratolytic agent; ciclopirox olamine; tolnaftate; undecylenic acid; flucytosine; griseofulvin; haloprogin and effective combinations of these.

Enzyme inhibiting compositions are substances that inhibit or prevent the biological activity of fecal enzymes that lead to skin irritation and/or diaper rash. It is believed, without being limited by theory, that fecal proteolytic and lipolytic enzymes, of intestinal and/or pancreatic origin, play a direct role in causing diaper rash and its associated, undesirable skin ailments. Enzyme inhibiting compositions suitable for use herein are not particularly limited, but generally include at least one enzyme inhibiting agent for neutralizing the enzymatic activity of at least one enzyme typically found in human feces. The enzyme inhibiting agent may be present in an amount of between 0.01 and 100 wt %. It is to be appreciated that the amount of enzyme inhibiting agent(s) may include any percentage in this range. Examples of enzyme inhibiting agents include, without limitation, hexamidine; triacetin; phytic acid; water soluble lipase inhibitors in the form of metallic salts such as zinc chloride; chelating agents such as ethylenediamine tetraacetic acid for restricting the availability of protease cofactors; esters of fatty alcohols; saturated, unsaturated, linear or branched zinc salts of a fatty acid of from 12 to 24 carbon atoms; aminated acylated acids such as propionylcysteine, propionylhydroxyproline or caproylcysteine; and effective combinations of these.

It may be desirable to optionally include active ingredients suitable for treating wounds such as burn or cuts. For example, antibacterial agents such as benzalkonium chloride, benzethonium chloride, methylbenzethonium chloride, phenol, povidone-iodine complex, chlorhexidene and derivatives (e.g., chlorhexidene gluconate), cetrimonium bromide, cetrimonium chloride, cetrimonium stearate, cetylpyridinium chloride, octenidine dihydrochloride, thymol, triclosan, and terpenes (e.g., tea tree oil) may be included in the personal care composition. Still other optional active ingredients include wound healing agents such as panthenol, pantothenic acid, calcium panththenate, grape seed extract, manuka honey, and ulmo honey. Further option ingredients include local anesthetics, sometimes referred to as numbing agents. Examples of numbing agents include lidocaine, benzocaine, novocaine, chloroprocaine, etidocaine, prilocalne, and ropivacaine.

The personal care compositions disclosed herein may include one or more pH buffers to maintain the composition at a desired pH. Typically, human skin has a pH of between 4 and 6 to provide an acidic environment that is deleterious to bacteria and other undesirable microbes that may be present on the surface of the skin. It is believed, without being limited by theory that effectively maintaining skin pH in its natural acidic state may also counteract the irritating effects of ammonia and potentially reduce the activity of fecal enzymes. In order for the skin to have good elasticity and act as a suitable barrier against infection, it is important to maintain the pH of the skin at its natural pH or pH range. Thus, it may be desirable to include a pH buffer in the personal care composition to provide a suitable pH or pH range, for example, between 4 and 7, or even 5.5. The pH buffer may be present in an amount of between 0.1 and 10 wt %. Suitable examples of pH buffers for use herein include, without limitation, citric acid, boric acid, lactic acid, glycolic acid, gluconic acid, malic acid, maleic acid, other fruit acids, potassium hydrogen phthalate, each of these in combination with their respective conjugate base, and mixtures thereof.

In certain embodiments, it may be important to include a humectant in the personal care composition. Humectants are substances known to readily absorb water, even from the air (i.e., they are hygroscopic). Examples of humectants include glycerine, polyglycerols, propylene glycol, ethylene glycol, glyceryl triacetate, polyethylene glycols, polypropylene glycols, and polyols such as sorbitol, glucose, fructose, and 1,5-pentylene diol. When the present personal care composition is dispensed from a container, residual amounts of skin care composition may remain around the dispensing opening of the container, depending on the type of container/dispenser. As the liquid components (if any) of this residual composition dry up, only the particulates are left (e.g., particles of zinc oxide). These particulates may clog or block a portion or all of the dispensing opening, which may undesirably interfere with future dispensing of the composition. By including a humectant in the skin care composition, any residual skin care composition present around the dispensing opening of the dispenser may stay sufficiently moist for up to 3, 7, 10, 14, or even 21 days or more, and thereby reduce the likelihood of a clog or undesirable blockage of the dispensing opening.

The personal care composition may include one or more anti-stick ingredients to reduce the tendency of certain contaminants to stick to the skin (e.g., dirt; bacteria; bodily exudates such as urine, feces, mucous, and blood; plaque; grease; food residue; and the like). The anti-stick ingredients may be present in an amount of between 0.1 and 100 wt %. Examples of anti-stick ingredients suitable for use herein include, without limitation, polyethylene glycols ("PEG") such at PEG-400, PEG-4000, triols such as glycerin, ethoxylated fatty alcohols such as steareth-50 and ceteth-150, ethoxylated fatty acids such as polyoxyethylene (100) stearate, propylene glycol, polypropylene glycol, sugars such as glucose and sorbitol, sugar based surfactants such as sorbitan esters and ethoxylated sorbitan esters, sucrose esters and ethoxylated sucrose esters and alkyl polyglycosides, diols such as hexylene diol, and PEG8 phosphate ester.

The personal care composition may include one or more other optional ingredients such as aroma therapy ingredients (e.g., chamomile), anti-oxidants (e.g., tocopherol), consumer recognized skin beneficial ingredients (e.g., aloe), preservatives (e.g., phenoxy ethanol), and stablizers (e.g., xanthan gum). Other examples of optional ingredients include, without limitation, lavender, oatmeal extract, vitamin E acetate, green tea extract, milk proteins, and calundula.

The personal care composition may include a carrier material. The carrier material provides a matrix in which the other ingredients of the personal care composition are dispersed and which helps to provide a relatively uniform distribution of the other personal care composition ingredients on the skin of a user. The carrier material may be present in an amount of between 1 and 99 wt %. Suitable examples of hydrophilic carrier materials include water, low molecular alcohols like ethyl alcohol, polyethylene glycols, propylene glycols, glycerin, and other low molecular weight diols, triols, and polyols that are liquids at room temperature. In certain instances, the carrier may also be an organic or silicone based carrier like mineral oil, isoparaffinic fluids like isododecane or isohexadecane or isoeicosanes or mixtures thereof, cyclopentasiloxane, low molecular weight silicone fluids like 10 centistoke dimethicone fluid, or esters like isopropyl myritate.

In order to provide a personal care composition that forms a suitable film layer on skin or other substrates and does not require additional manipulation after being applied (e.g., spreading with the hands or fingers), it is important that the skin care composition have a proper balance of viscosity, surface tension, and droplet size. These properties may be influenced by the ingredients of the composition as well as the structural properties of the container. For example, the personal care composition may require a high enough viscosity to keep the individual ingredients of the composition from separating out, but sufficiently low enough to permit the composition to be easily dispensed. Further, the nozzle shape and/or size may impact the viscosity of the composition as it exits the container (e.g., non-Newtonian fluids may experience the commonly known phenomenon of shear thickening or shear thinning). Thus, suitable viscosities range from 50 to 5000 centipoise ("cP"), from 200 to 2500 cP, or even from 500 to 1500 cp when measured at 22 C with a DV-III+Rheometer (available from Brookfield Inc.) using a RV#3 spindle rotating at 30 RPM. Similarly, it is important that the surface tension of the personal care composition be high enough to form droplets when dispensed from a container as intended and to keep the composition from "running" once it is applied to the skin, but low enough to provide sufficiently small droplets. If the droplets are too big, the applied composition may not appear as a suitable film on the skin but rather as a multitude of individual droplets. In addition, large droplet sizes may be an indication of an unstable composition (e.g., prone to separation). A user or caregiver who perceives a multitude of droplets as opposed to a film may attempt to further spread out the droplets, resulting in undesirable contamination of a hand, finger(s), and/or other surface or substrate used to spread the composition. Suitable droplet sizes for the dispensed compositions disclosed herein may be from 100 nm to 100 μm. For effective wetting, spreading, and/or adhesion to a surface such as skin, the surface tension of the composition to be applied should be lower than that of the surface to which it is applied. Depending on the actual conditions of humidity and temperature, the surface tension of human skin is typically between 38 mN/m and 56 mN/m. Thus, the surface tension of a composition suitable for applying to skin (i.e., exhibits desirable wetting, spreading and/or adhesion to skin) would be below a surface tension in this range. But the surface tension of the composition should not be so low as to promote excessive spreading of the composition on the surface to which it is applied (e.g., on the skin and/or surface of a diaper). For example, a suitable surface tension for a personal care composition applied to skin may be less than 56 mN/m to promote wetting and adhesion to the skin, but greater than 30 mN/m to avoid excessive spreading of the composition on the skin (e.g., between 35 and 40 mN/m).

Container

When treating and/or trying to prevent certain skin ailments, as well as applying any composition to a surface, it may be important to apply the composition as a film to obtain the full potential of the benefit provided by the composition. As pointed out above, spreading or rubbing of the composition to form a suitable film may result in undesirable contamination or require the use of an additional applicator. Thus, a container that is capable of dispensing a composition such that a film is formed on a surface to which the composition is applied, without the need for additional manipulation on the part of a user, addresses a long felt need in the art.

FIG. 1A shows an exemplary embodiment of a container preform 10. The container preform 10 is shown as being inserted into a top portion of a mold 30 such as, for example, the type of mold used in a blow molding or injection molding process. The container preform 10 may include a polymeric preform 12 and an elastically deformable band 14, which at least partially surrounds a portion or even all of the polymeric preform 12. The elastic band 14 may be joined to the polymeric preform 12 by any means commonly known in the art, as long as it does not undesirably interfere with the ability of the polymeric preform and/or the elastic band 14 to expand and/or collapse. The polymeric preform 12 may be elastically or plastically extensible and is configured to receive a flowable composition such as, for example, one or more of the personal care compositions disclosed herein. In certain embodiments, the polymeric preform 12 may be expanded to form a collapsible bag (e.g., by filling or partially filling the polymeric preform 12 with a gas and/or a personal care composition). The polymeric preform 12 and/or the band 14 may be expanded such that sufficient potential energy is stored in the stretched elastic band 14 and/or collapsible bag to expel at least some or substantially all of the skin composition stored in the collapsible bag in the manner intended. For example, the potential energy stored in the elastic band 14 may be sufficient to expel a liquid composition stored in the expanded polymeric preform a distance of between 30 centimeters ("cm") and 125 cm, for example, between 40 and 100 cm, between 50 and 80 cm, or even between 60 and 70 cm, when the composition has a viscosity of between 50 and 5000 cP when measured at 22 C with a DV-III+ Rheometer (available from Brookfield Inc.) using a RV#3 spindle rotating at 30 RPM.

The polymeric preform 12 may be made of a flexible, extensible, and, optionally, elastic material. Examples of materials suitable for forming the polymeric preform 12 include, without limitation, nylon; polypropylene; polyethylene; low density polyethylene; polybutylene; polyester (e.g., polyethylene terephthalate); high density polyethylene (HDPE); polyamide-based materials; acrylonitrile materials; and combinations of these. Particularly suitable examples are SARANEX brand plastic resin available from DOW Chemical Company, Midland Mich. and BAREX 218 brand thermoplastic acrylic resin available from BP Chemicals Corporation, Ohio. The polymeric preform 12 may be formed of two or more materials, for example, during a co-extrusion blow molding process. In certain embodiments, the material used to form the polymeric preform 12 is relatively inert, such that there are substantially no undesirable tastes or smells imparted to the contents of the collapsible bag. Further, an inert polymeric preform 12 may inhibit or even prevent certain ingredients from undesirably migrating into the collapsible bag from the skin care composition and vice versa. For example, certain skin care compositions use preservatives to increase the effective life of the skin composition. If these preservatives were to migrate out of the skin care composition and into the material of the collapsible bag, the skin care composition might be undesirably affected (e.g., become rancid), such that it does not deliver its expected benefit to a user or exhibits undesirable characteristics (e.g., foul odor or change in appearance). The polymeric preform 12 may be flexible over substantially its entire surface in both the radial and axial dimensions, except that it may be desirable to provide some amount of stiffness in the neck region 13. In certain embodiments, it may even be desirable to provide a polymeric preform 12 that is stiff enough over its entire length to be self-supporting. The walls of the polymeric preform 12 may be of any suitable thickness, as desired. For example, the polymeric preform 12 may have an average wall thickness of from 1.5 mm to 9.5 mm; or even 3.2 mm before it is stretched and an average sidewall thickness of from 25.4 micrometers ("µm") to 50.8 µm when fully expanded (e.g., 30.5 µm to 46 µm) over substantially its entire length except, optionally, at the neck region 13. The portion of the polymeric preform 12 that forms the neck region 13, which can be within 2.5 cm of the valve member 16 when the polymeric preform 12 is expanded, may be thicker. It is to be appreciated that minor variations in thickness at any given cross-section of the polymeric preform are contemplated herein, and are within the scope and spirit of the present disclosure.

Figure 12:
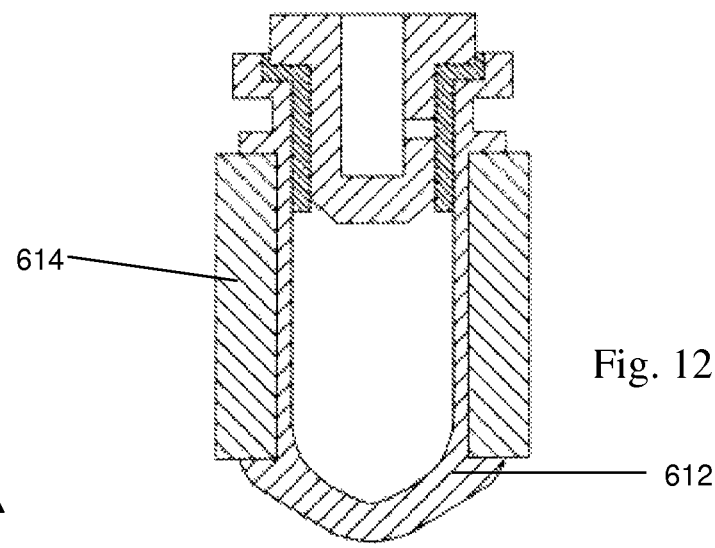
FIGS. 12 and 13 illustrate exemplary dimensional changes that may occur after transitioning a container preform into a collapsible bag.
Figure 13:
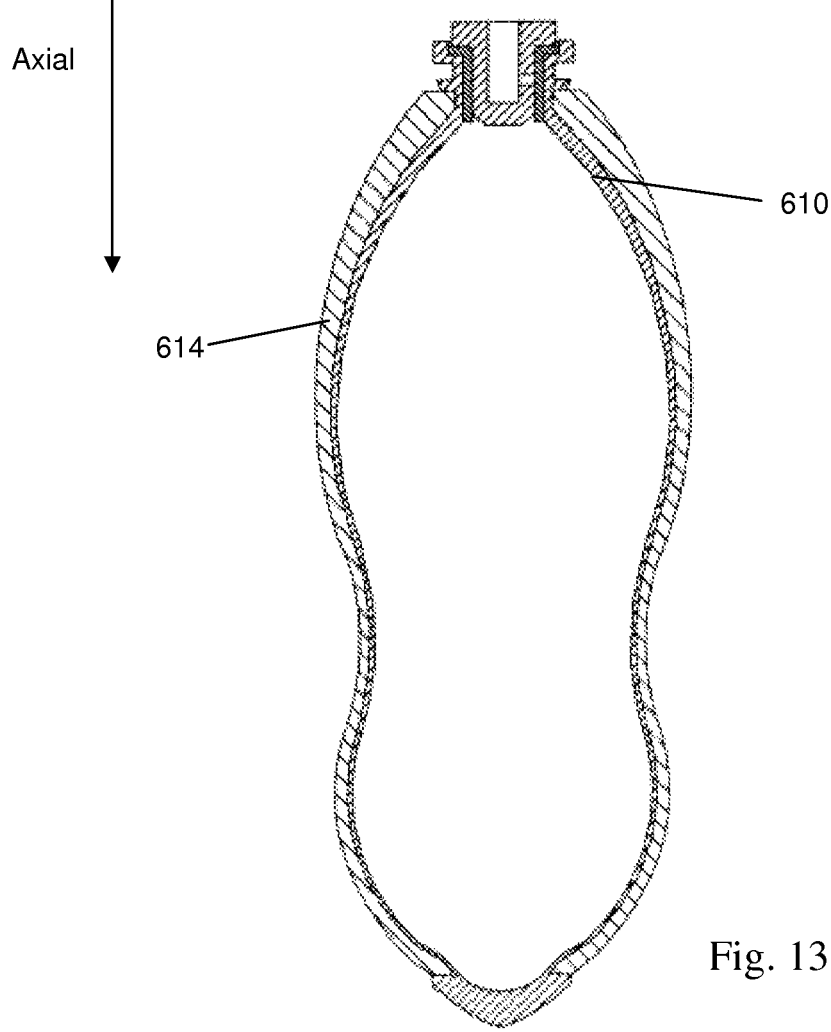

When making the container preform 10, it may be desirable to heat the polymeric preform 12 prior to stretching and/or receiving the skin care composition. It is believed, without being limited by theory, that heating the polymeric preform 12 and/or elastic band 14 softens and/or increase the pliability of the preform 12 and/or band 14. In certain embodiments, all or at least a portion of the polymeric preform 12 may be heated to a temperature ranging from 0.5 to 15° C., or from 5 to 10° C. above the glass transition temperature ("$T_g$") of the polymeric preform 12. In another embodiment, the elastic band 14 may also be heated to the same temperature. Heating may be done by transmitting IR or other electromagnetic radiation through the elastic band 14 to the polymeric preform 12. Pressure is applied to the interior of polymeric preform 12 to plastically or elastically expand the polymeric preform 12 into a collapsible bag and elastically expand the elastic band 14. This pressure can be provided by a pressurized gas (e.g., air or nitrogen), a driven rod or other physical member, insertion of a skin care composition, or a combination of these. In one embodiment, the applied pressure is from 150 kPa to 1000 kPa, or even 584 kPa. Without intending to be limited by theory, it is believed that an applied pressure of within ±200 kPa; ±180 kPa; or even ±160 kPa of 584 kPa may be particularly suitable for expending the polymeric preform 12 quickly and uniformly, without undesirably damaging the polymeric preform 12 or elastic band 14. The volume of the polymeric preform 12, when expanded is not particularly limited and may be, for example, between 100 ml and 1 liter (e.g., 200 ml, 500 ml, 750 ml). The elastic band is capable of stretching axially and/or radially at least 50% up to more than 750% of its initial unstretched length and/or width. FIGS. 12 and 13 illustrate, by way of example, the difference in size of the elastic band 614 and the polymeric preform 612/collapsible bag 610 in an unstrained state (i.e., FIG. 12) as compared to a stretched state (i.e., FIG. 13). Similarly, during use, the elastic band 614 may shrink or contract in an axial and/or radial direction from 50 to 95% from an initial dispensing at first use to a final, complete dispensing when the product is operatively exhausted. Because of the potential for significant axial expansion and contraction of the elastic band 614, the length of the polymeric preform 612 can be significantly greater than the length of the elastic band 614 in its unstrained/unstretched state. For example, the polymeric preform 612 can be at least about 100%, 150%, 200%, or 300% of the length of the associated and unstrained elastic band 614. Exemplary methods for providing suitable axial expansion of the elastic band 614 are disclosed in co-pending U.S. Ser. No. 12/604,965 filed by Chan, et al., on Oct. 23, 2009.

The potential energy created due to the expansion of the elastic band 14 is generally sufficient to collapse the collapsible bag 18 once the internal pressure of the blow molding process is removed. After the polymeric preform 12 is expanded into a collapsible bag 18 and subsequently collapsed, it may be charged with a flowable personal care composition. During this filling process, the collapsed bag expands both radially and axially, which causes the elastic band 14 to expand, and potential energy is once again created due to the expansion of the elastic band 14. A normally-closed valve member 16 may be joined with the filled bag to provide an openable/closable pathway for the skin care composition to flow through, but to prevent the potential energy stored in the elastic band 14 from undesirably acting on the filled collapsible bag 18 and urging the skin care composition out of the collapsible bag 18.

Figure 1B:
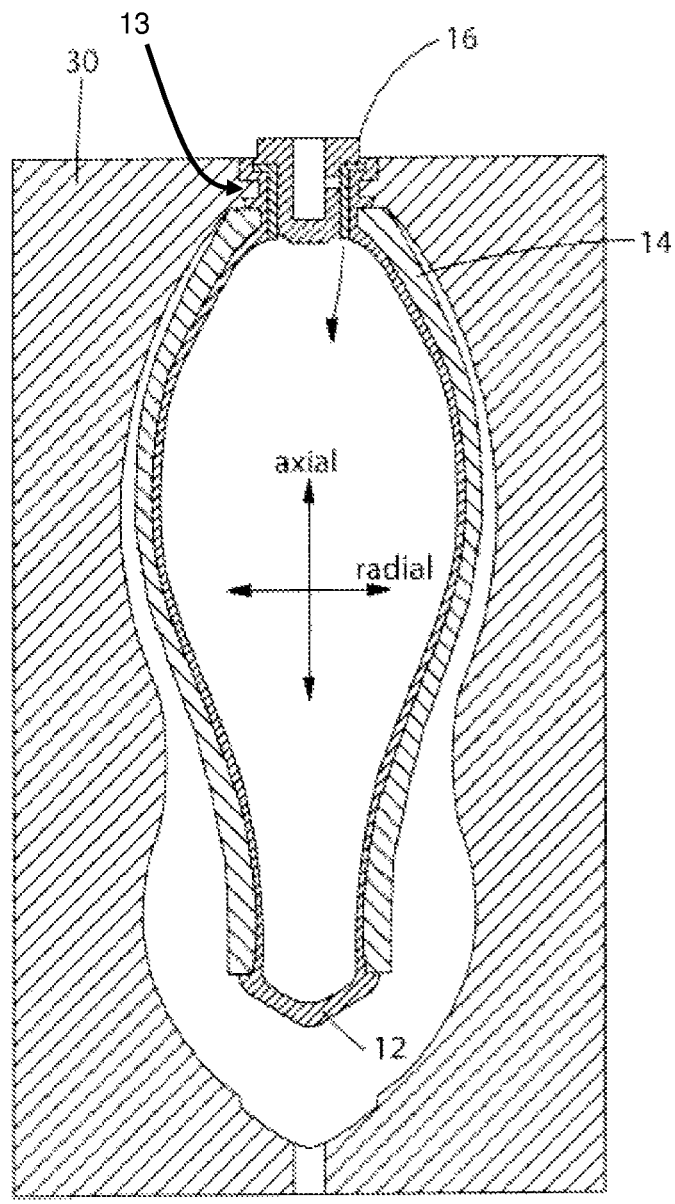
Figure 1C:
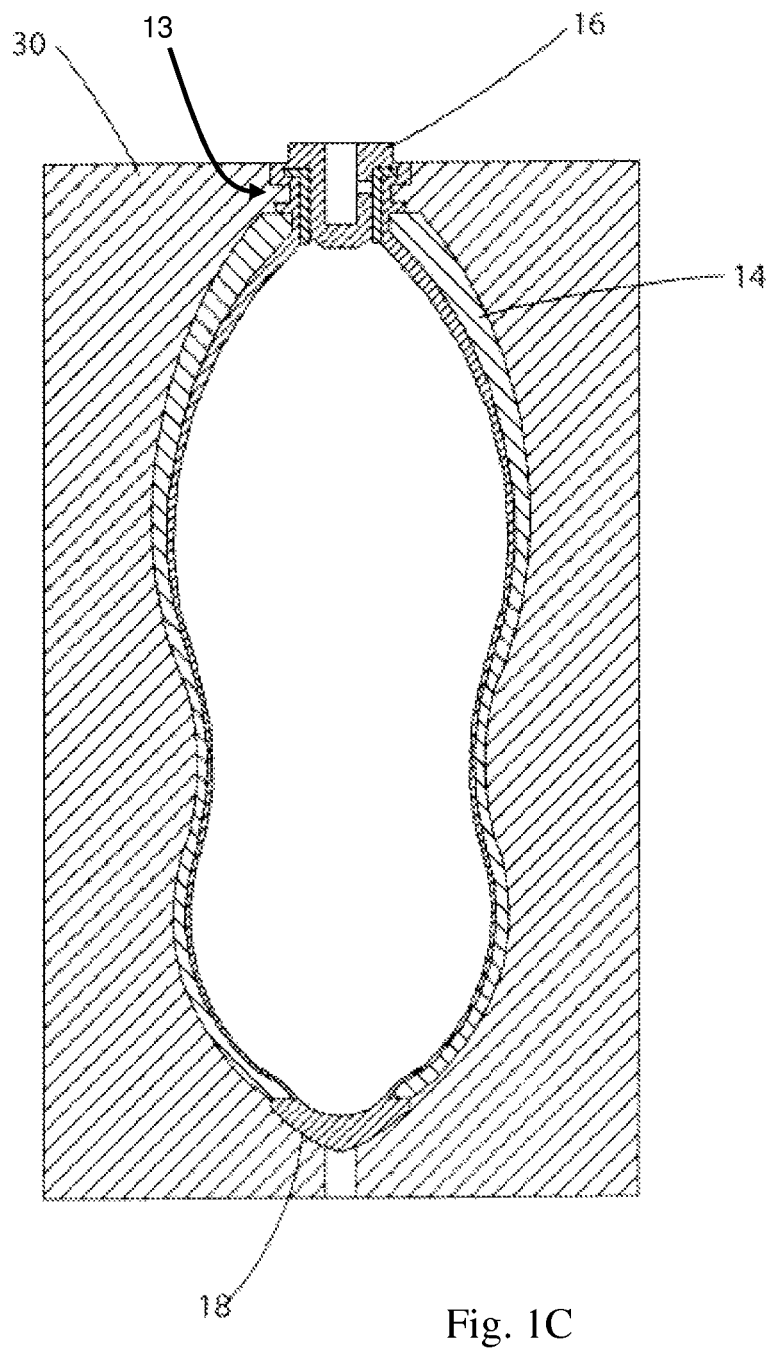

The elastically deformable band 14 may be formed from an elastically extensible material (e.g., natural rubber, synthetic rubber, and/or a thermoplastic elastomer). Suitable natural rubbers include those which have a tensile strength of at least 24.1 megapascals ("MPa"). Additionally the natural rubber may have a hardness (Shore A) of between 30 and 40, and a 100% Modulus of up to 862 kilopascals ("kPa"). Suitable methods for determining the properties of a rubber material such as those disclosed herein are disclosed in ASTM No. D 412-06a$^{e2}$, titled "Standard Test Methods for Vulcanized Rubber and Thermoplastic Elastomers." The elastically deformable band 14 may be formed, for example, from a natural rubber made from a rubber plant (e.g., Guayule shrub or Hevea tree) or a natural rubber modified with latex additives. The elastic band 14 may be formed as a unitary sleeve (e.g., as shown in FIGS. 1A-1C) or formed as one or more discrete bands of elastic material joined to the polymeric preform 12. The elastic band 14 may be configured to provide a uniform or non-uniform pressure to different portions of the collapsible bag 18. For example, several discrete elastic bands of varying thickness may be positioned at different locations on the collapsible bag 18. The thicker band(s) may provide more pressure to the portion of the collapsible bag 18 to which it(they) are joined relative to the thinner band(s). The pressure generated by the elastic bands may depend upon, among other things, their thickness, the modulus of the material from which they are formed or a combination thereof.

The elastically deformable band 14 may be free or substantially free of carbon black or any other ingredients which would unduly obstruct or interfere with the transmittance of a particular wavelength or wavelengths of electromagnetic radiation. For example, it may be desirable to configure the elastic band 14 such that IR radiation is able to pass through all or at least a portion of the elastic band 14. IR transparency provides the unique benefit of allowing the simultaneous heating of the elastic member 14 and the polymeric preform 12, which may reduce manufacturing complexity and/or cost relative to known containers and methods of making such containers. In certain embodiments, the elastic band 14 may be configured to pass different wavelengths, intensities, and/or combinations of electromagnetic radiation (e.g., UV, visible light, microwave, radio frequency, and/or x-ray radiation).

FIG. 1B shows an exemplary embodiment of a partially expanded container preform 10. The polymeric preform 12 and elastic band 14 are shown expanding both axially and radially. In certain embodiments, the polymeric preform 12 is expanded plastically and the elastic band 14 is expanded or stretched elastically. The potential energy generated as a result of stretching the elastic band may be sufficient to generate 1000 kPa or less of hydrostatic pressure, for example, less than 340 kPa; 310 kPa, or even less than 240 kPa, but more than 100 kPa on the collapsible bag 18 and/or contents thereof. The pressure generated by the elastic band may depend upon, among other things, the thickness of the elastic band, the modulus of the material from which the elastic band is formed, or a combination thereof. That is, the thicker the elastic band, the more potential energy it is capable of generating when stretched. A substantially uniform elastic band 14 suitable for use herein, when relaxed, may have an average wall thickness of between 1 and 10 mm. The same elastic band 14, when stretched to accommodate an expanded collapsible bag 18 as intended (e.g., as shown in FIG. 1C), may have an average wall thickness of from 100 μm to 400 μm; or from 180 μm to 240 μm, or even from 200 μm to 220 μm.

FIG. 1C shows an example of a fully expanded polymeric preform 12. The polymeric preform 12 and elastic band 14 extend all the way to the walls of the mold 30 to define a collapsible bag 18 and/or a container. If the internal pressure is released from the collapsible bag 18, the potential energy associated with the elastic band 14 will act on the collapsible bag 18 to at least partially collapse it in both the axial direction and radial directions.

Figure 2:
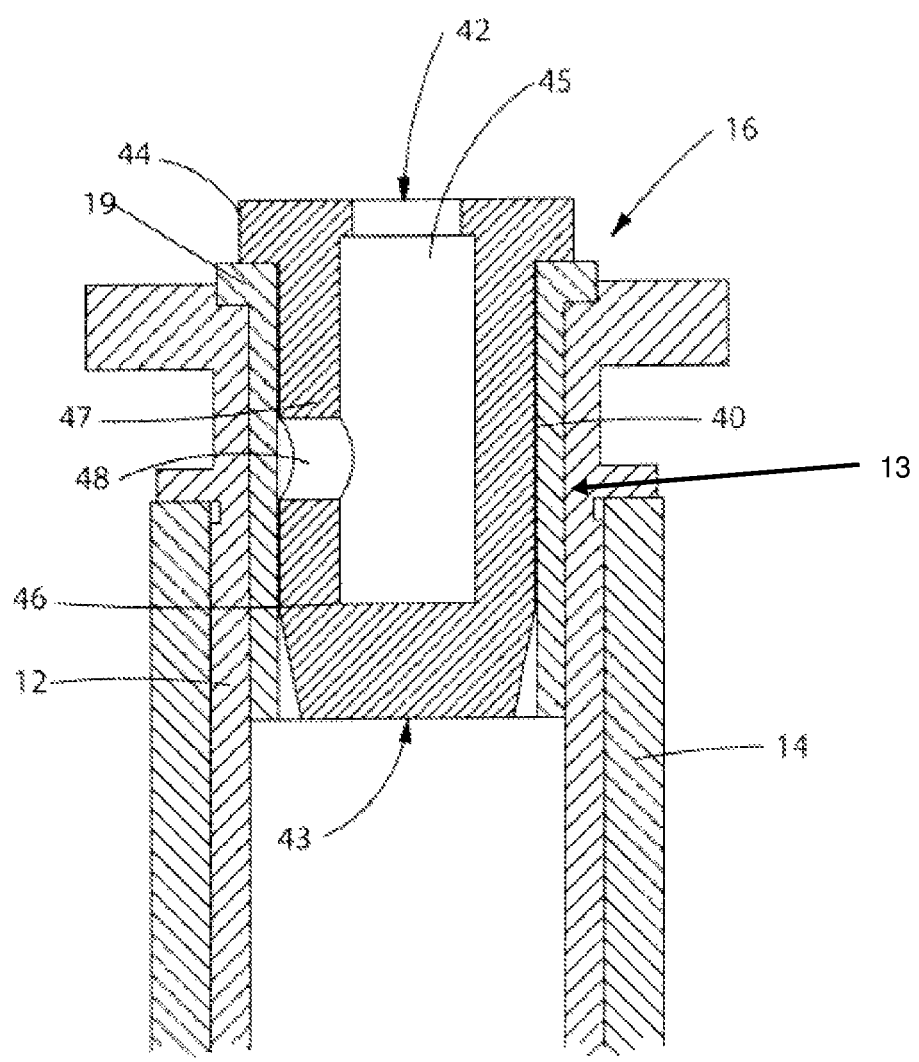
FIG. 2 is a partial cross-section view of a valve member inserted into an opening of a container preform.

Prior art containers may utilize a variety of different valve assemblies to provide an openable and/or closable flow path to dispense flowable contents stored in the container. Some of these valves utilize a complex arrangement of parts (e.g., ferrules, coil springs, valve seating members, snap rings) that can add difficulty and expense to a manufacturing process. In contrast, the container disclosed herein may include a relatively simple valve member 16. FIG. 2 shows an exemplary valve member 16 suitable for use herein. The valve member 16 may include an elastically deformable body 40 in cooperation with a rigid insert 19. The elastically deformable body 40 may be made from any suitable elastomeric material commonly known in the art. In certain embodiments, an inner wall of the polymeric preform 14 or the neck region 13 may be used to functionally replace the insert 19. The insert 19 (or alternatively a neck region 13 of the polymeric preform 12) may be configured to function as a sleeve to seal the valve 16 in its normally closed position. The valve body 40 may include an open end 42, an opposing closed end 43, and a flange 44 disposed proximate to the open end 42. In certain embodiments, a blind hole 45 (i.e., a hole that does not extend completely through the valve member 16) extends from the open end 42 and terminates at a blind hole bottom 46. As shown in FIG. 2, the blind hole 45 defines the inner surface of the valve body side wall 47. A through-hole 48 may extend from the inner surface to the outer surface of the side wall 47 (i.e., extends completely through the side wall 47) and is positioned between the open end 42 and the bottom 46 of the blind hole 45. In certain embodiments, the valve 16 may include no blind holes 45 and two or more through holes 47 arranged to provide a flow path. The body 40 and/or through-hole(s) 48 may be arranged to form a seal with the wall of the insert 19. The insert 19 may made from a rigid material such as, for example, plastic, metal, hard elastomers, glass, and cardboard or other cellulosic based materials to provide a desirable sealing surface. The valve member 16 may be actuated by a user, for example, by applying a sufficient amount of axial stress to elastically deform the valve body 40 such that the valve body 40 becomes elongated and its diameter is reduced. A fluid flow channel may then be formed between the exterior surface of body 40 and the insert 19 as the body 40 is elongated and reduced in diameter. The fluid flow channel, once created, permits the passage of fluid from the interior of the collapsible bag to the external environment by way of through-hole 48, blind hole 45, and open end 42. Other examples of suitable valve members for use herein are disclosed in co-pending U.S. Ser. No. 12/604,931 filed by Chan, et al., on Oct. 23, 2009.

Figure 3:
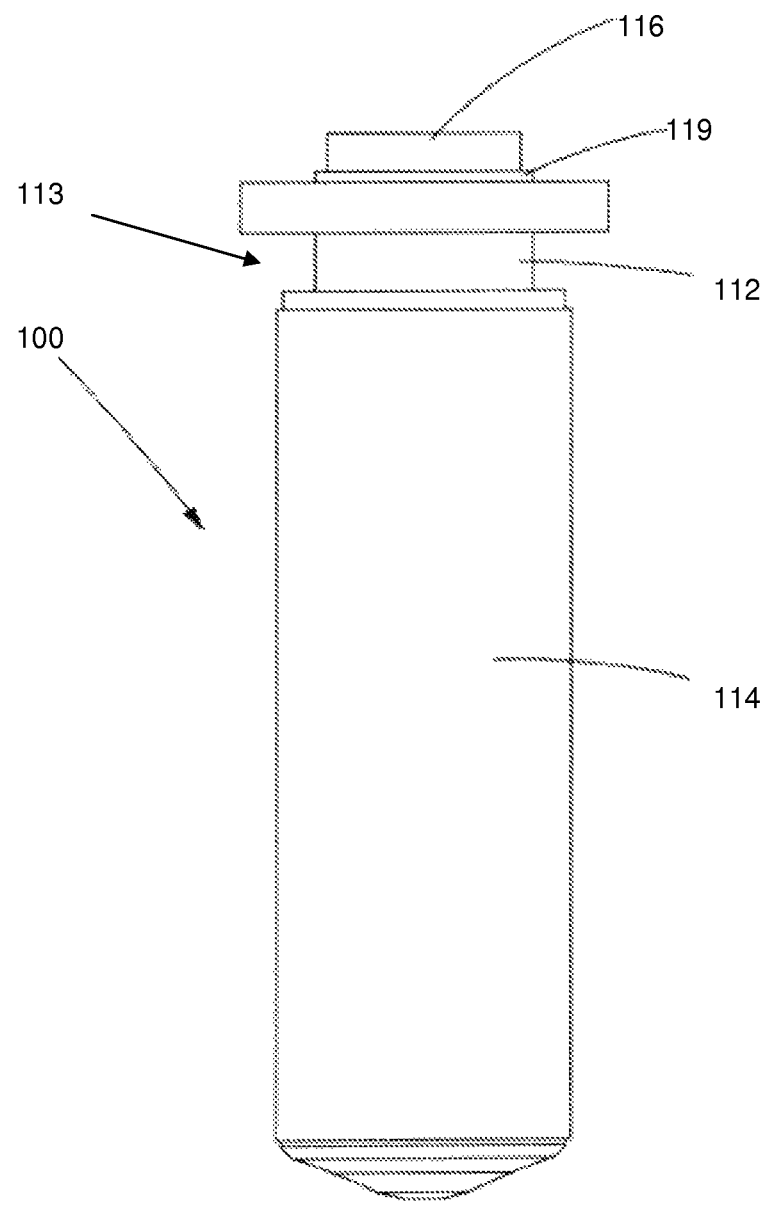
FIG. 3 is a side view of an exemplary container preform.
Figure 4:
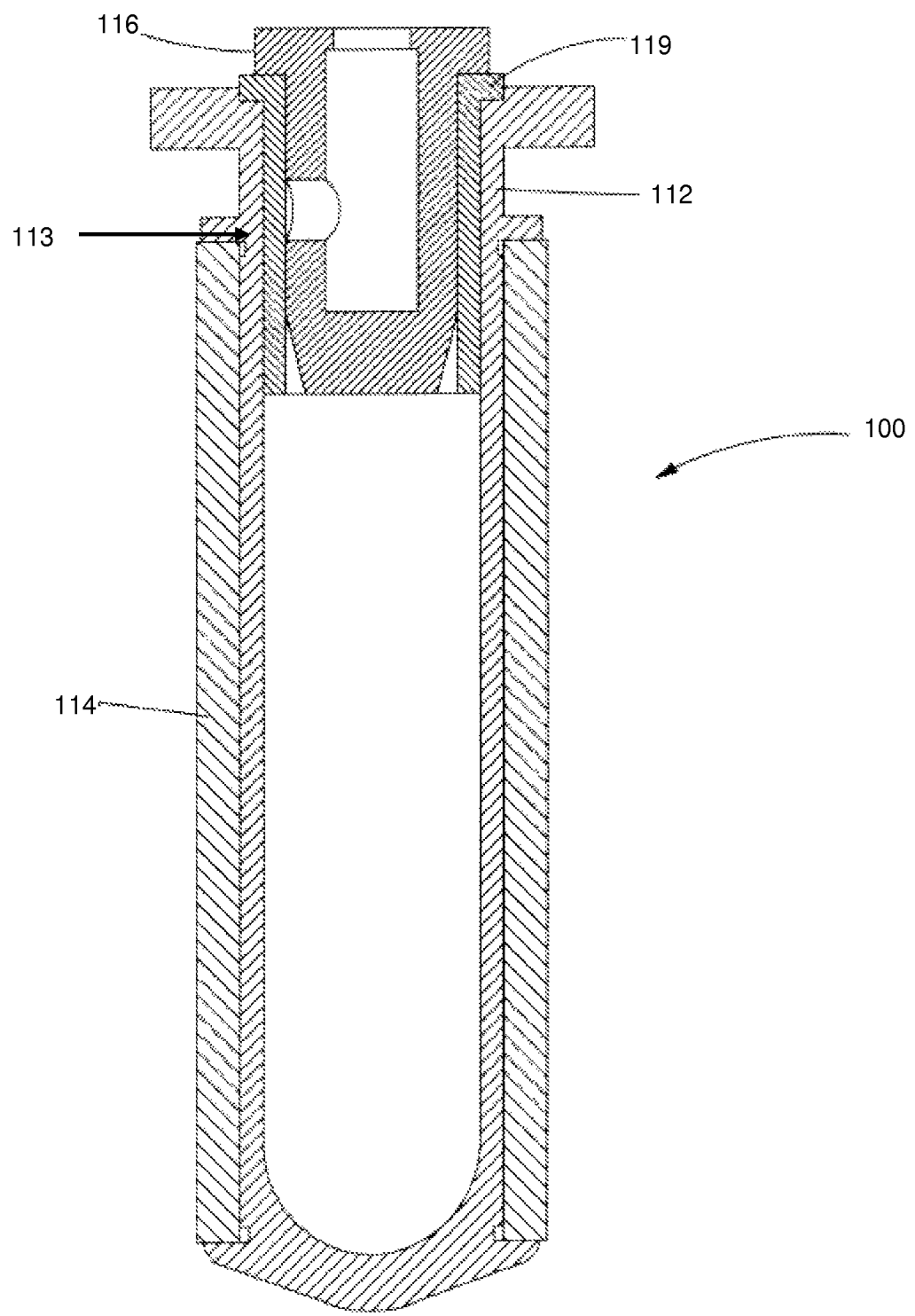
FIG. 4 is a cross-section view of the exemplary container preform shown in FIG. 3.

FIG. 3 shows another exemplary embodiment of a container preform 100. The container preform 100 includes a polymeric preform 112, an elastically deformable band 114, valve member 116, and an optional adapter/insert 119 disposed between valve member 116 and a neck region 113 of polymeric preform 112. FIG. 4 shows an axial cross-section view of the container preform 10 of FIG. 3.

Figures 5, 6:
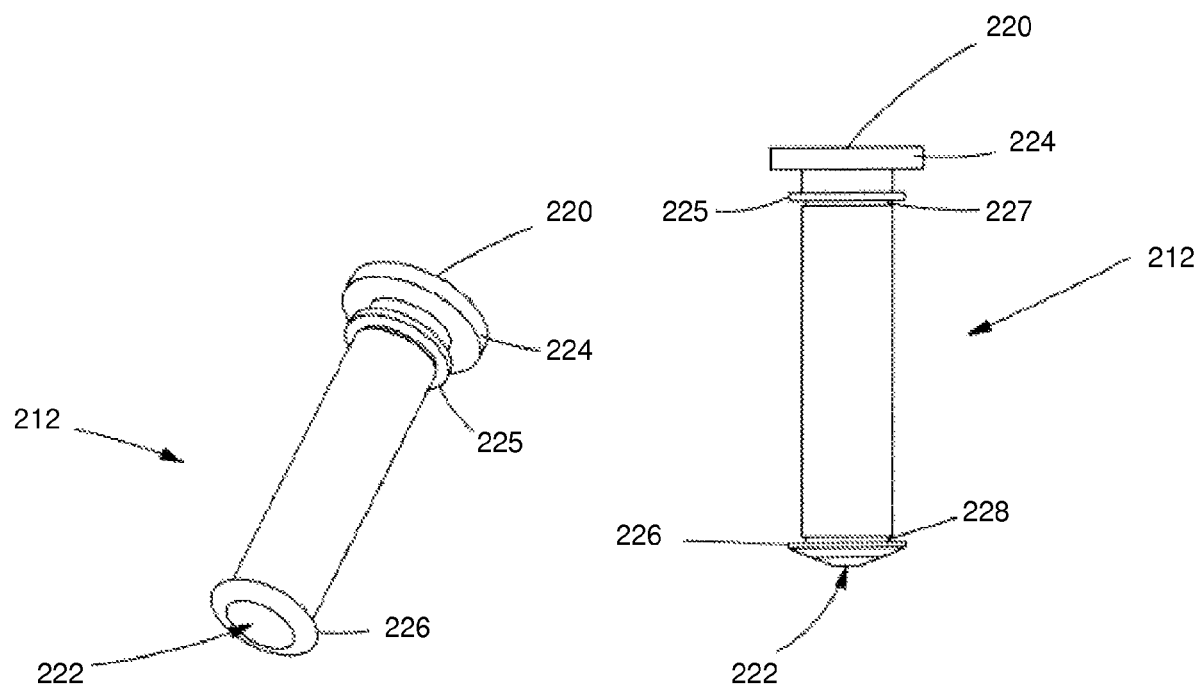
FIG. 5 is a perspective view of an exemplary polymeric preform.
FIG. 6 is a side view of the exemplary polymeric preform shown in FIG. 5.

FIGS. 5 and 6 show an exemplary embodiment of a polymeric preform 212. The polymeric preform 212 includes an open end 220 (although the actual opening is not shown) and an opposing closed end 222. The polymeric preform 212 may include a flange 224 proximate to the open end 220 to help hold the polymeric preform 212 in a particular position in a blow mold. The flange 224 may also be used for joining the expanded polymeric preform 212 to an outer container and/or a portion of a valve or actuator assembly. Additional flanges 225 and 226 and grooves 227 and 228 may be included to help position and retain the elastic band 214 in a variety of configurations, as desired. For example, the elastic band 214 may be joined to the polymeric preform 212 at one or more points proximate to the open end 220 and/or closed end 222. In certain embodiments, an adhesive may be placed in the grooves 227 and/or 228 to affix the elastic band 214 to the polymeric preform 212. The grooves 227 and 228 may be configured for receiving adhesive, but it should be appreciated that the adhesive could also be deposited on the exterior of the polymeric preform 212 in the absence of any specific receiving feature such as the optional grooves 227 and 228. Nonlimiting examples of adhesives suitable for use herein include epoxies, urethanes, acrylates, and/or other adhesives capable of suitably bonding an elastically deformable material with a plastic material. The adhesive may be air-cured, light-cured, and/or cured via chemical cross-linking. Particularly suitable examples of adhesives for use herein are LOCTITE 4306 and 4307 brand light-cured adhesives and LOCTITE 406, 4501, and 495 brand adhesives, all available from Henkel, located in Germany. In certain embodiments, the elastic band 214 is not affixed to the polymeric preform 212 at points which are positioned away from the ends 220 and 222 of the polymeric preform 212 (i.e., points that are spaced significantly from the open end 220 and the closed end 222) so that the polymeric preform 212 walls may expand to the blow mold boundary as effectively and efficiently possible without being constrained by the elastic band 214. Mechanical means may also be employed to join the elastic band 214 to polymeric preform 212. Alternatively or additionally, the elastic band 214 may be configured such that it is unnecessary to affix the distal portion of the band to the polymeric preform 212.

Figure 7:
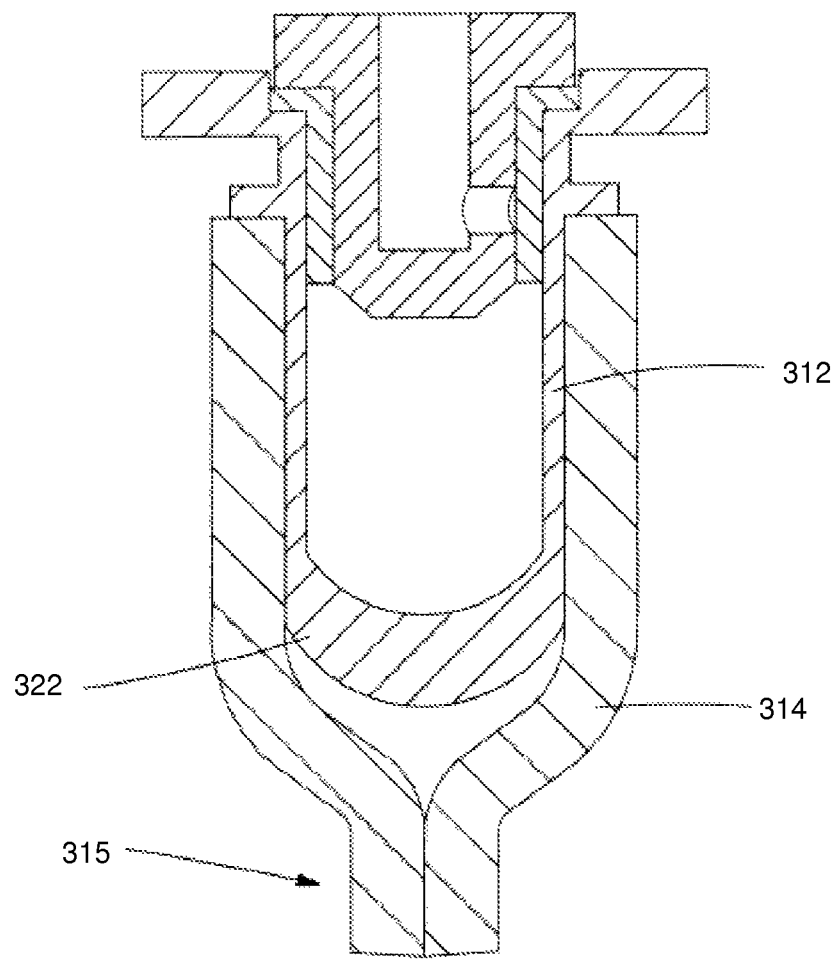
FIG. 7 is a cross-sectional view of an exemplary embodiment of a container preform.

FIG. 7 shows an exemplary embodiment wherein the elastic band 314 has a distal end 315 that is closed over the closed end 322 of the polymeric preform 312. When the polymeric preform 312 expands axially, for example, during blow molding, the elastic band 314 can correspondingly stretch in the axial direction. The closed distal end 315 may be formed by adhesively adhering inner wall portions of the elastic band 314 to one another. Alternatively or additionally, a restraining member (e.g., a clamp) may be placed around the exterior of the distal end 315 to hold it closed. Although the distal end 315 is shown completely closed, it may also be partially closed or be manufactured to have a smaller opening than its opposing side so that the polymeric preform 312, and any collapsible bag that may be blow molded from the polymeric preform 312, do not push through the distal end 315 of the elastic band 314.

Figure 8:
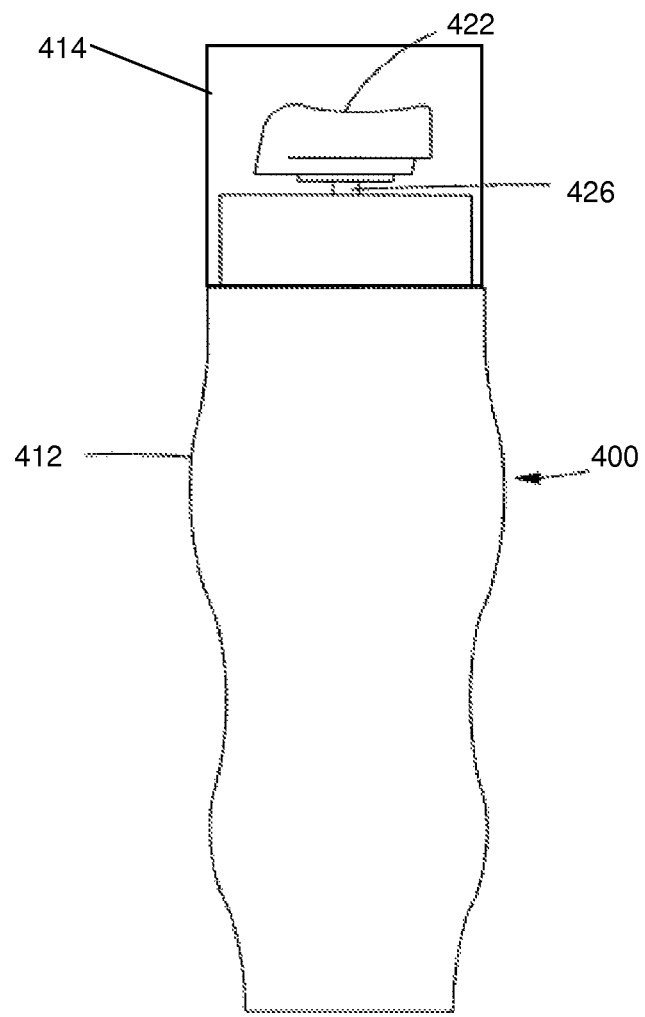
FIG. 8 is a side view of a skin care product.
Figure 9:
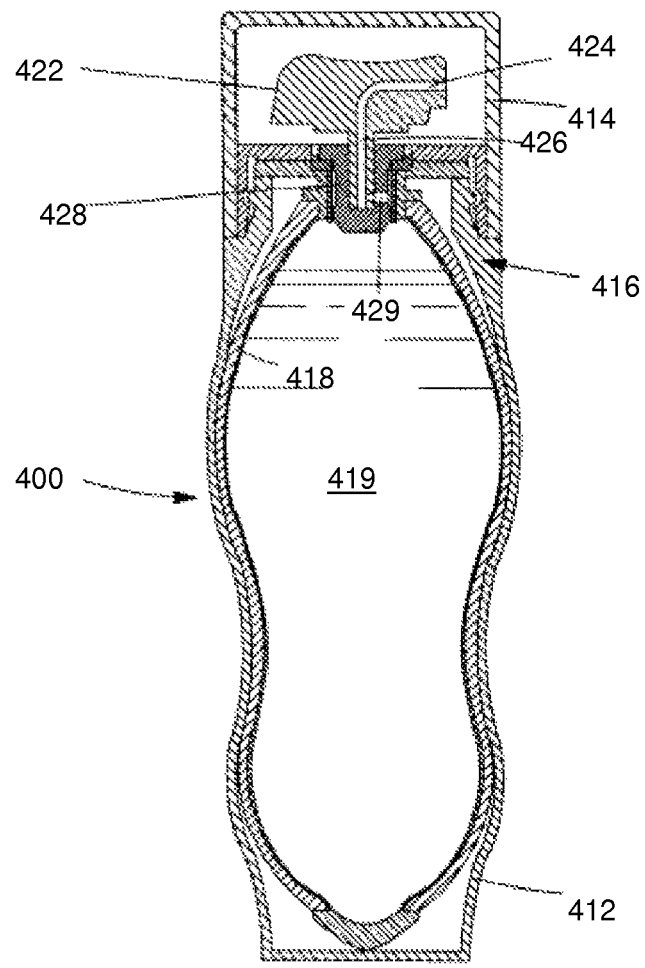
FIG. 9 is a cross-section view of the skin care product of FIG. 8.
Figure 10A:
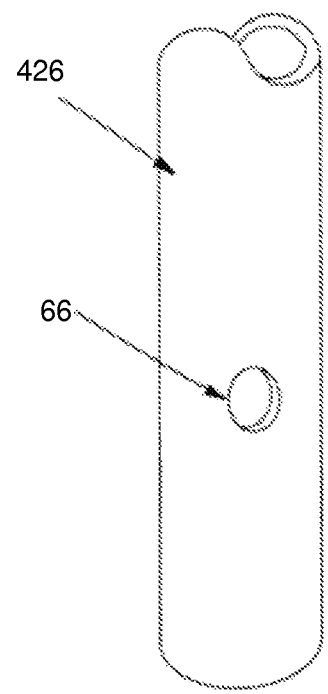
FIGS. 10A and 10B are side views of two exemplary tubes.
Figure 10B:
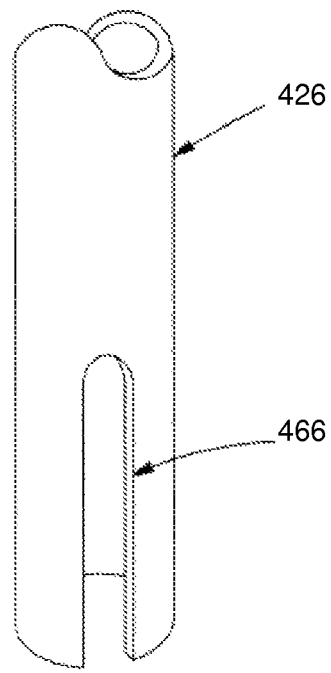

An exemplary personal care product 400 is shown in FIG. 8. FIG. 9 shows an axial cross-section view of the personal care product 400 of FIG. 8. The personal care product 400 includes a shaped container 412 and overcap 414. The overcap 414 shown in FIG. 8 is transparent, but it is to be appreciated that the overcap 414 may be translucent or even opaque. A material dispensing system 416 is disposed within container 412, which includes a collapsible bag 418 formed from a polymeric preform such as one of the polymeric preforms disclosed herein. The collapsible bag 418 is filled with a flowable personal care composition 419. An actuator 422 is positioned on container 412 and includes a flow path defined at least partially by a tube 426. The tube 426 may be connected to an elastically deformable valve member 428. Downward displacement of tube 426 positions valve member 428 such that a volume of the personal care composition 419 is capable of passing into the through-hole 429, which may be aligned with a second through-hole and/or an open-ended slot (e.g., FIG. 10A shows a second through-hole 66 on tube 426 and FIG. 10B shows an open-ended slot 466 on tube 426) on tube 426, such that the personal care composition 419 is capable of flowing through the length of the tube 426 and exiting the package 410. In certain embodiments, the tube 426 may be rotatable within the valve member 428 such that in one position a first through-hole 66 is aligned with a second through-hole 429 and in another position it is not. This feature may provide a desirable locking aspect to prevent or limit the discharge of composition 419 if the actuator is inadvertently hit or pressed.

In certain embodiments, it may be desirable to dispense the personal care composition in a particular pattern (e.g., cone-shaped, planar, single-stream, multi-stream, or amorphous); droplet size; at a particular pressure; and/or range (i.e., effective distance that the dispensed composition can travel). For example, the container may include a nozzle with an opening configured to dispense a personal care composition in a cone-shaped pattern that has an effective area of coverage of between 2.54 cm$^2$ and 15.24 cm$^2$; between 5.08 cm$^2$ and 10.16 cm$^2$; or even between 7 cm$^2$ and 9 cm$^2$ when the nozzle is held at a distance of between 15.24 cm and 30.48 cm away from the skin. In certain embodiments, the person care composition may be dispensed in a spray pattern that has an effective area of coverage of between 1 cm$^2$ and 225 cm$^2$. Further, in certain embodiments, it may be important to size the dispenser opening such that the particles in certain particle containing personal care compositions do not agglomerate at the opening and clog the dispenser. The personal care product disclosed herein, when used as intended, enables a user to apply a substantially uniform film of personal care composition to the skin of a recipient without the need for further manipulation of the composition by the user or recipient (e.g., no need to further spread or rub the composition). In addition to configuring the personal care composition to have a suitable viscosity and surface tension, it is important to provide a nozzle that has an opening(s) that is/are configured to apply the composition to a surface in the form of a suitable film. For example, the nozzle opening may be configured to provide a particular pressure drop (i.e., the difference between the pressure exerted on the composition in the container and the pressure at which it is applied to a surface) and/or shear rate. By selectively configuring the opening, the shear rate, for example, can be controlled to minimize the undesirable effect(s) of shear thickening or shear thinning on the composition.

Figure 11:
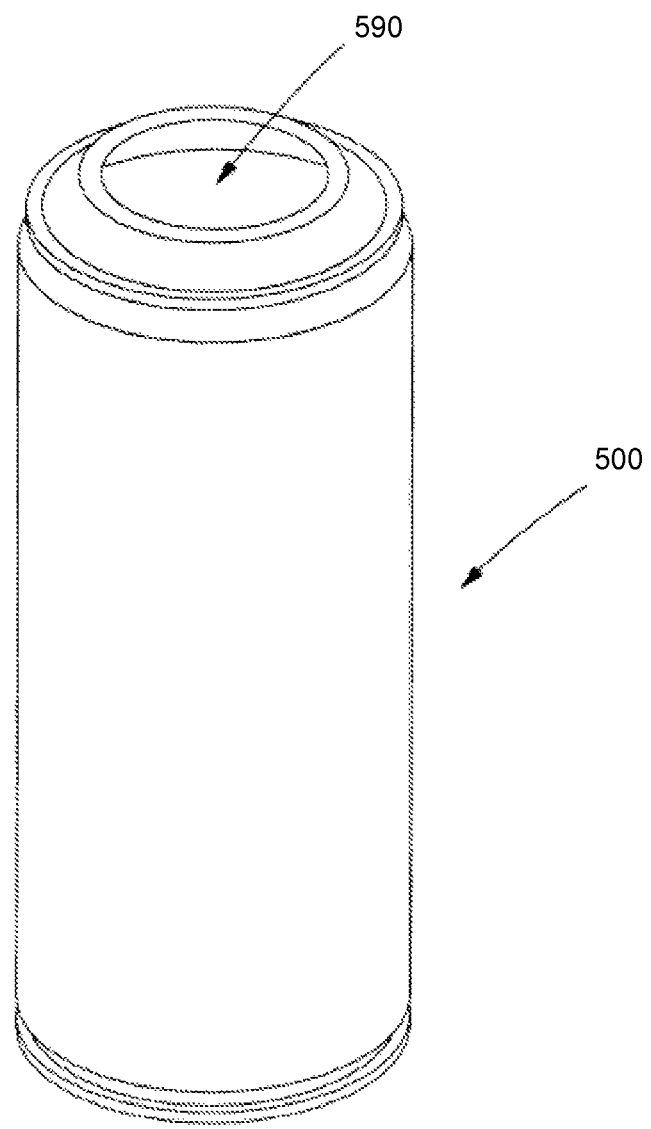
FIG. 11 is a perspective view of a container.

FIG. 11 shows an exemplary embodiment of an outer container 500 suitable for use herein. The outer container 500 may include an opening 590 at the top of the container for inserting a polymeric preform, collapsible bag, and/or valve member. The outer container 500 may be made of any suitable material known in the art. In certain embodiments, the outer container 500 may be formed from the same material as the polymeric preform. Examples of methods for making personal care products are disclosed in the copending U.S. application titled "METHOD FOR MAKING A PERSONAL CARE PRODUCT," identified as P&G Docket No. 11694, and filed on Apr. 26, 2010 by Klofta, et al.

EXAMPLES

Examples of personal care compositions are provided below. The compositions are prepared according to standard preparation methods commonly known in the art. These exemplary compositions may be used in conjunction with the tube-in-sleeve style containers described above. The composition listed as Example 1 has a viscosity of 1050 cP when measured at 22 C with a DV-III+Rheometer (Brookfield Inc.) using a RV#3 spindle rotating at 30 RPM.

Example 1

| Ingredient | Alternate Name | wt % |
|---|---|---|
| Water | | 80.99% |
| Disodium EDTA | | 0.10% |
| Sodium Benzoate | | 0.12% |
| Avicel PC591 | Microcrystalline Cellulose & Cellulose Gum | 1.20% |
| Xanthan Gum | | 0.18% |
| Finsolv TN | C12-15 Alkyl Benzoate | 1.20% |
| High Oleic Sunflower Oil | Helianthus Annuus (Sunflower) Seed Oil | 2.00% |
| PDMS (200 cStk) | Dimethicone | 0.80% |
| Cetyl Alcohol | | 0.30% |
| Brij72 | Steareth-2 | 0.51% |
| Brij78 | Steareth-20 | 0.31% |
| Glycerin | | 1.02% |
| Euxyl PE9010 | Phenoxyethanol & Ethylhexylglycerin | 0.30% |
| Benzyl Alcohol | | 0.30% |
| ZnO (USP from USZinc) | Zinc Oxide | 10.05% |
| Hexamidine Diisethionate | | 0.10% |
| Vitamin E | Tocopherol | 0.10% |
| Aloe | Aloe Barbadensis | 0.01% |
| Avenalipid | Avena Sativa (Oat) Kernel Oil | 0.01% |
| Exalitode Scent | | 0.05% |
| Citric Acid | | 0.35% |

Example 2

| Ingredient | wt % |
|---|---|
| Mineral Oil | 57.10% |
| Sunflower Oil | 22.00% |
| Kraton RP-6917 | 5.00% |
| ZnO | 12.00% |
| Beeswax | 2.00% |

| Ingredient | wt % |
| --- | --- |
| Dimethicone | 0.90% |
| Olive Butter | 0.50% |
| Tocopherol | 0.50% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care product for applying a personal care composition to skin in the form of a film without the use of an additional applicator, the personal care product comprising:
   a. an outer container;
   b. an at least partially expanded collapsible bag disposed in the outer container, an elastic member surrounding at least a portion of the collapsible bag such that the elastic member is stretched axially and radially, the elastic member being constructed of an elastically extensible material that permits the transfer of infrared radiation through at least a portion of the elastic member; and
   c. a personal care composition disposed in the collapsible bag;
   d. wherein the personal care composition has at least one of a viscosity of between 50 and 5000 cP and a surface tension of between 30 and 56 mN/m; and
   e. wherein the personal care composition is dispensed as a multitude of droplets having an average droplet size of between 1 and 100 micrometers.

2. The personal care product of claim 1, wherein the composition includes at least one of a skin care composition, an antifungal composition, an antimicrobial composition, a wound healing composition, and an enzyme inhibiting composition.

3. The personal care product of claim 2, wherein the personal care composition includes a skin care composition and at least one active ingredient selected from the group consisting of zinc oxide, petrolatum, white petrolatum, mineral oil, cod liver oil, lanolin, dimethicone, vitamin A, palmitate, allantoin, calamine, kaolin, glycerin, colloidal oatmeal, and combinations thereof.

4. The personal care product of claim 2, wherein the personal care composition includes an antifungal composition and at least one active ingredient selected from the group consisting of natamycin, rimocidin, nystatin, amphotericin B, candicin, hamycin, imidazoles, triazoles, thiazoles, allylamines, echinocandins, benzoic acid in combination with a keratolytic agent, ciclopirox olamine, tolnaftate, undecylenic acid, flucytosine, griseofulvin, haloprogin, and effective combinations of these.

5. The personal care product of claim 2, wherein the personal care composition includes an enzyme inhibiting composition and at least one active ingredient selected from the group consisting of hexamidine; triacetin; water soluble lipase inhibitors in the form of metallic salts; chelating agents that restrict the availability of protease cofactors; esters of fatty alcohols; saturated, unsaturated, linear, or branched zinc salts of a fatty acid of from 2 to 22 carbon atoms; aminated acylated acids; and effective combinations of these.

6. The personal care product of claim 1, wherein the collapsible bag comprises at least one section having a wall thickness of less than about 100 micrometers.

7. The personal care product of claim 1, wherein the collapsible bag has an open end and a closed end opposite said open end, and the elastically extensible band comprises a first end proximate the bag open end and a second end that is joined to the bag proximate the bag closed end.

8. The personal care product of claim 1, wherein the elastic member is joined to the collapsible bag by at least one of an adhesive, a mechanical fastener, or a combination thereof.

9. The personal care product of claim 1, wherein the elastic member exerts a hydrostatic pressure of between 135 and 480 kilopascals on the collapsible bag.

10. The personal care product of claim 1, wherein at least 95% of the personal care composition disposed in the collapsible bag is dispensed when the product is operatively exhausted.

11. The personal care product of claim 1, wherein the elastic member has a stretched length and an unstretched length, and the stretched length is at least 50% greater than the unstretched length.

12. An article for applying a composition to a surface in the form of a film without the use of an additional applicator, the product comprising:
   a. an outer container;
   b. an at least partially expanded collapsible bag disposed in the outer container, an elastic member surrounding at least a portion of the collapsible bag such that the elastic member is stretched axially and radially, the elastic member being constructed of an elastically extensible material that permits the transfer of infrared radiation through at least a portion of the elastic member; and
   c. a flowable composition disposed in the collapsible bag;
   d. wherein at least 95% of the composition disposed in the collapsible bag is dispensed when the article is operatively exhausted.

13. The article of claim 12, wherein the collapsible bag includes a bag open end and a bag closed end, the article further comprising a valve member disposed in the bag open end, the valve member providing a flow path for the flowable composition to flow out of the collapsible bag.

14. The article of claim 13, wherein the valve member includes a rigid insert and a flexible body member operatively configured to provide an openable/closable flowpath through the valve member.

15. The article of claim 14, wherein the valve member includes at least one of a through hole and a blind hole.

16. The article of claim 12, wherein the collapsible bag is formed by expanding a polymeric preform and the collapsible bag has a volume that is at least 100% greater than a volume of the polymeric preform.

17. The article of claim 16, wherein the collapsible bag has a volume that is between 10 times and 100 times greater than the volume of the polymeric preform.

* * * * *